(12) United States Patent
Kreischer

(10) Patent No.: US 9,176,510 B2
(45) Date of Patent: Nov. 3, 2015

(54) VOLTAGE EQUALIZATION DEVICE AND A MEDICAL IMAGING DEVICE HAVING A VOLTAGE EQUALIZATION DEVICE

(71) Applicant: Ludwig Kreischer, Dormitz (DE)

(72) Inventor: Ludwig Kreischer, Dormitz (DE)

(73) Assignee: SIEMENS AKTIENGESELLSCHAFT, München (DE)

( * ) Notice: Subject to any disclaimer, the term of this patent is extended or adjusted under 35 U.S.C. 154(b) by 476 days.

(21) Appl. No.: 13/744,739

(22) Filed: Jan. 18, 2013

(65) Prior Publication Data

US 2013/0187622 A1   Jul. 25, 2013

(30) Foreign Application Priority Data

Jan. 20, 2012   (DE) .......................... 10 2012 200 784

(51) Int. Cl.
| | |
|---|---|
| G05F 1/14 | (2006.01) |
| H02M 1/10 | (2006.01) |
| A61B 5/055 | (2006.01) |
| G01R 33/36 | (2006.01) |

(52) U.S. Cl.
CPC . G05F 1/14 (2013.01); A61B 5/055 (2013.01); G01R 33/36 (2013.01); H02M 1/10 (2013.01)

(58) Field of Classification Search
CPC ............. G05F 1/10; G05F 1/14; G05F 1/147; G05F 1/153; G05F 1/16; G05F 1/20; G05F 1/22; G01R 33/36; A61B 5/055; H02M 1/10
USPC .................... 323/247, 255–258; 363/142, 143
See application file for complete search history.

(56) References Cited

U.S. PATENT DOCUMENTS

| | | | | |
|---|---|---|---|---|
| 3,818,321 | A * | 6/1974 | Willner et al. ................ | 323/258 |
| 5,408,171 | A * | 4/1995 | Eitzmann et al. ............. | 323/258 |
| 7,800,349 | B2 * | 9/2010 | Tsang et al. .................. | 323/255 |
| 8,203,319 | B2 * | 6/2012 | Fujita et al. .................. | 323/255 |
| 2011/0316498 | A1 * | 12/2011 | Lee et al. ...................... | 323/258 |

FOREIGN PATENT DOCUMENTS

| | | |
|---|---|---|
| DE | 405075 C | 10/1924 |
| DE | 1952796 A1 | 4/1971 |
| DE | 3721591 A1 | 1/1989 |

* cited by examiner

*Primary Examiner* — Jessica Han

(57) ABSTRACT

A voltage equalization device for equalizing voltage fluctuations in a voltage supply is provided. The voltage supply has an electrical voltage that is as constant as possible. The voltage equalization device has at least one transformer unit which has a primary winding unit and a secondary winding unit and, on one of the two winding units, has at least three or more selection units for switching in or switching out turns of the winding unit. Two adjacent selection units are so arranged in each case as to be separated from one another by a distance having a number of turns. The number of turns between two first adjacent selection units is different from the number of turns between two further adjacent selection units.

16 Claims, 6 Drawing Sheets

VOLTAGE EQUALIZATION DEVICE AND A MEDICAL IMAGING DEVICE HAVING A VOLTAGE EQUALIZATION DEVICE

CROSS REFERENCE TO RELATED APPLICATION

This application claims priority of German application No. 10 2012 200 784.9 filed Jan. 20, 2012, which is incorporated by reference herein in its entirety.

FIELD OF INVENTION

The present application relates to a voltage equalization device for equalizing voltage fluctuations in order to provide a voltage supply having an electrical voltage that is as constant as possible. The voltage equalization device has at least one transformer unit which has a primary winding unit and a secondary winding unit and, on one of the two winding units, has at least three or more selection units for switching in or switching out turns of the winding unit that has the selection units. Two adjacent selection units are so arranged in each case as to be separated from one another by a distance having a number of turns.

BACKGROUND OF INVENTION

Medical imaging devices such as e.g. magnetic resonance imaging devices are required to be connected to different voltage supply networks throughout the world, e.g. to voltage supply networks having nominal voltages between 380 V and 480 V. However, an actual voltage of these voltage supply networks can deviate in this case by up to 10% from the nominal voltage during everyday operation. A further problem exists here in that when current is drawn off in these voltage supply networks a further voltage drop occurs due to an only finitely small internal mains supply resistance. Said further voltage drop is estimated to be 5% of the nominal voltage, for example.

In order to solve this problem, power supply equipment for magnetic resonance imaging devices is already known in the prior art in which a transfer ratio of a power supply transformer is changed by switching in or switching out turns at a primary winding unit in such a way that a supply voltage which is present at a secondary winding unit remains as constant as possible. For this purpose, the mains supply transformer has taps that are arranged at an equal distance from one another. In this case the switching in and/or switching out of individual turns of the primary winding unit can be effected by changing the tap connections or by using regulated electronic mains supply components and/or by electronic switching units that can be actuated electromotively and/or automatically. For example, a controller can effect a selection for a switching unit here by measuring a mains supply voltage that is currently present and/or by comparing the voltage that is present on the secondary side of the transformer with a reference value. However, the quality of the voltage stabilization here depends on the number of switching units that can be switched.

It is also known to tolerate dynamic deviations from a set nominal voltage, such as e.g. fluctuations in the supply network, in most cases by configuring redundancy in a gradient coil unit and/or in a radio-frequency antenna unit. Thus, for example, the gradient coil unit and/or the radio-frequency antenna unit can be designed for a maximum permitted voltage which still allows operation of the gradient coil unit and/or the radio-frequency antenna unit at a maximum overvoltage, while sufficient power reserves are still present in respect of a slew rate or a pulse power in the case of a minimum undervoltage. However, the overdimensioning of the gradient coil unit and/or the radio-frequency antenna unit involves significant additional costs here in comparison with an optimal design of the gradient coil unit and/or the radio-frequency antenna unit.

SUMMARY OF INVENTION

The object of the present application is to provide a compact and economical voltage equalization device which has a wide equalization range for a voltage that is required to be set to constant in the event of voltage fluctuations. The object is achieved by the features recited in the claims.

The application takes as its starting point a voltage equalization device for the purpose of equalizing voltage fluctuations in order to provide a voltage supply having an electrical voltage that is as constant as possible, said voltage equalization device comprising at least one transformer unit which has a primary winding unit and a secondary winding unit and, on one of the two winding units, has at least three or more selection units for switching in or switching out turns of the winding unit that has the selection units, wherein two adjacent selection units are so arranged in each case as to be separated from one another by a distance comprising a number of turns.

It is proposed that the number of turns between two first adjacent selection units should be different from the number of turns between two further adjacent selection units. By the embodiment according to the application it is possible to switch different distances—such as different numbers of turns—between two selection units. This means that different voltage values at the further winding unit can be set by the at least three or more selection units at the winding unit having the selection units. A voltage $U_2$ that is present at the further winding unit is determined as follows:

$$U_2 = U_1 * N_2 / N_1,$$

where $N_2$ is the number of turns at the further winding unit here, $N_1$ is the number of active turns or switched-in turns at the winding unit having the selection units, and $U_1$ is the voltage that is present at the switched-in turns or active turns at the winding unit having the selection units. By the different distances between the individual selection units it is possible to achieve a wide and variable adjustment range for a voltage that is present at the further winding unit. The setting range and/or adjustment range of the voltage that is present at the further winding unit is dependent in this case on the number of selection units and the number of turns between the individual selection units relative to one another. The smaller the distance or number of turns between the individual selection units here, the more finely it is possible in this case to set a voltage that is present at the further winding unit by switching in and/or switching out turns using the selection units. In addition to this, the voltage equalization device can be kept compact by virtue of the different distances of the individual selection units relative to one another, thereby saving further construction costs. The first two adjacent selection units and the two further adjacent selection units can have at most one shared selection units in this case. The individual selection units have an electronically actuatable switch unit in each case, thereby allowing rapid switching-in or switching-out of turns at the winding unit having the selection units, such that rapid setting of a voltage value (such as a constant voltage) at the further winding unit can be achieved.

The selection units can be arranged at the primary winding unit or at the secondary winding unit. In a development, however, the selection units are arranged at the primary winding unit, such that a setting range for setting the voltage that is present at the secondary winding can be extended effectively. If the secondary winding unit has a greater number of turns than the primary winding unit, for example, there is little benefit in an arrangement at the secondary winding unit.

It is further proposed that the winding unit having the selection units should have an upper winding end and a lower winding end, and that at least two of the selection units should be arranged at the upper winding end and at least two of the selection units should be arranged at the lower winding end. This allows a wide adjustment range to be realized on account of possible combinations between the selection units arranged at the upper winding end and/or the selection units arranged at the lower winding end.

In a development of the application it is proposed that the selection units arranged at the upper winding end should be so arranged as to be separated from one another by an identical number of turns, and that the selection units arranged at the lower winding end should be so arranged as to be separated from one another by an identical number of turns, wherein the number of turns between the selection units arranged at the upper winding end is different from the number of turns between the selection units arranged at the lower winding end. A wide setting range with fine gradation can be achieved using a combination of one or more of the selection units arranged at the upper winding end and/or one or more of the selection units arranged at the lower winding end.

In a development the number of turns between the individual selection units arranged at a lower winding end is formed by the number of selection units arranged at an upper winding end multiplied by the number of turns between two adjacent selection units arranged at the upper winding end. In this way it is possible to prevent an identical number of turns by different combinations comprising a switched-in selection units arranged at the upper winding end in each case and a switched-in selection units arranged at the lower winding end in each case. Moreover, it is possible to achieve a maximum setting range offering maximum scope for variation in terms of the number of active turns and/or the number of turns between which the voltage is present at the winding unit having the selection units, for the purpose of setting a voltage, such as a constant voltage, that is present at the further winding unit, such as the secondary winding unit.

In a further embodiment of the application it is proposed that the selection units should in each case have an electronically actuatable switch unit which can be switched between a low-impedance switch position and a high-impedance switch position, whereby a structurally simple and economical voltage equalization device can be achieved. It is furthermore possible to achieve a rapid setting of the number of turns at the winding unit having the selection units, and hence a setting of the voltage, such as a constant voltage, that is present at the further winding unit, such as the secondary winding unit. In this context a low-impedance switch position is understood to mean that the selection units in this switch position establishes a connection, which is conductive during the operation of the voltage equalization device, to the turns that can be switched using this selection units, such that the voltage which is present at the winding unit having the selection units is present at these turns during the operation of the voltage equalization device. A high-impedance switch position in this context is understood to mean that the selection units in this switch position interrupts a connection, which is conductive during the operation of the voltage equalization device, to the turns that can be switched using this selection units, such that the voltage which is present at the winding unit having the selection units is not present at these turns.

In order to set the voltage effectively it is for only one of the selection units arranged at an upper winding end and only one of the selection units arranged at a lower winding end in each case to be disposed in the low-impedance switch position for the voltage supply. In this way it is possible to achieve an effective current flow within the winding unit having the selection units, and also to prevent a short-circuit, e.g. as a result of connecting two or more of the selection units switched-in at the upper winding end and/or two or more of the selection units switched-in at the lower winding end.

A wide range of possible combinations for combining the individual selection units can be achieved if a maximum number of combinations that can be set, for different numbers of turns between one of the selection units arranged at the upper winding end and one of the selection units arranged at the lower winding end at the winding unit having the selection units, is formed by the number of selection units arranged at an upper winding end of the winding unit, multiplied by the number of selection units arranged at the lower winding end of the winding unit. The individual combinations that can be set for different numbers of turns between a selection units arranged at the upper winding end and a selection units arranged at the lower winding end are independent of one another. Starting from a total number of selection units, it is also possible to achieve a maximum of possible combinations if the number of selection units arranged at the upper winding end and the number of selection units arranged at the lower winding end are as far as possible equal.

In a further embodiment of the application it is proposed that the selection units should in each case have an electronically actuatable switch unit that can be switched between two low-impedance switch positions, such that a minimum number of selection units can be used to achieve a wide setting range for an active number of turns at which is present the voltage that is present at the winding unit having the selection units. This also allows the voltage equalization device to be configured in a compact and economical manner. In a first of the two low-impedance switch positions of the electronically actuatable switch unit, the selection units establishes a connection, which is conductive during the operation of the voltage equalization device, to the turns that can be switched using this selection units, such that the voltage which is present at the winding unit having the selection units is present at these turns during the operation of the voltage equalization device. If the selection units is in the further low-impedance switch position, a connection, which is conductive during the operation of the voltage equalization device, to the turns that can be switched using this selection units is interrupted, such that the voltage which is present at the winding unit having the selection units is not present at said turns. In this further low-impedance switch position, provision is additionally made for switching or establishing a connection, which is conductive during the operation of the voltage equalization device, to a next adjacent selection units. It is here that in order to provide the voltage supply an arbitrary number of selection units from a total number of selection units can be concurrently switched to the switch position in which a conductive connection is established to the turns that can be switched using the selection units.

It is further proposed that the voltage equalization device should have a monitoring unit that determines a voltage characteristic at the winding unit having the selection units, and sets a switch position for the individual selection units. In this way the number of windings at the winding unit having the selection units can be set rapidly and it is possible to respond rapidly to a voltage change of a voltage supply network. As a result of this it is also possible to maintain a constant voltage at the further winding unit, such as the secondary winding unit.

It is further proposed that the monitoring unit should determine the voltage characteristic for one phase of a multiphase supply network and set a voltage for each of the phases of the multiphase supply network on the basis of the voltage characteristic that has been determined in respect of a single phase. The voltage equalization device has a plurality of transformer units for this purpose, such that a dedicated transformer unit is available for setting the constant voltage for each phase of the supply network. By the embodiment according to the application it is easy to set the required voltage value on the basis of the voltage that is present at the winding unit having the selection units, without any need for further components. The setting can be effected in this case by a controller and/or by a regulator, wherein the monitoring unit regulates the voltage that must be set for a phase of the multiphase supply network by selecting a respective switch position of the individual selection units as a function of the voltage characteristic that has been determined in respect of a single phase. In this way a current measured variable can be used at all times for the selection of the switch position of the selection units, and it is possible at the transformer unit to provide a voltage setting which can respond rapidly and automatically to voltage fluctuations.

The application also takes as its starting point a medical imaging device, such as a magnetic resonance imaging device, having a voltage equalization device for the purpose of equalizing voltage fluctuations in order to provide a voltage supply having a voltage that is as constant as possible, comprising at least one transformer unit which has a primary winding unit and a secondary winding unit and, on one of the two winding units, has at least three or more selection units for switching in or switching out turns of the winding unit that has the selection units, wherein two adjacent selection units are so arranged in each case as to be separated from one another by a distance comprising a number of turns.

According to the application it is proposed that the number of turns between two first adjacent selection units should be different from the number of turns between two further adjacent selection units. It is possible to set different distances—such as different numbers of turns—between two selection units, and different voltage values at the further winding unit can be set by the at least three or more selection units at the winding unit having the selection units. By the different distances between the individual selection units it is possible to achieve a wide and variable adjustment range for a voltage that is present at the further winding unit. The setting range and/or adjustment range of the voltage that is present at the further winding unit is dependent in this case on the number of selection units and the number of turns between the individual selection units relative to one another. The smaller the distance or number of turns between the individual selection units here, the more finely it is possible in this case to set a voltage that is present at the further winding unit by switching in and/or switching out turns using the selection units. In addition to this, the voltage equalization device can remain compact by virtue of the different distances of the individual selection units relative to one another, thereby saving further construction costs.

It is also proposed that the voltage equalization device should be designed for the purpose of setting a constant voltage for a gradient coil unit. This embodiment of the medical imaging device, such as a medical imaging device that is configured as a magnetic resonance imaging device, makes it possible to economize the structural space and the costs associated with an overdimensioned embodiment of the gradient coil unit. It is also possible to simplify the overall power supply of the remaining medical imaging device if the voltage equalization device is also designed for the purpose of setting a voltage for the remaining medical imaging device, such as e.g. by a further transformer unit.

BRIEF DESCRIPTION OF THE DRAWINGS

Features and details of the application will be revealed by the embodiments described below and with reference to the drawings, in which.

DETAILED DESCRIPTION OF INVENTION

Figure 1:
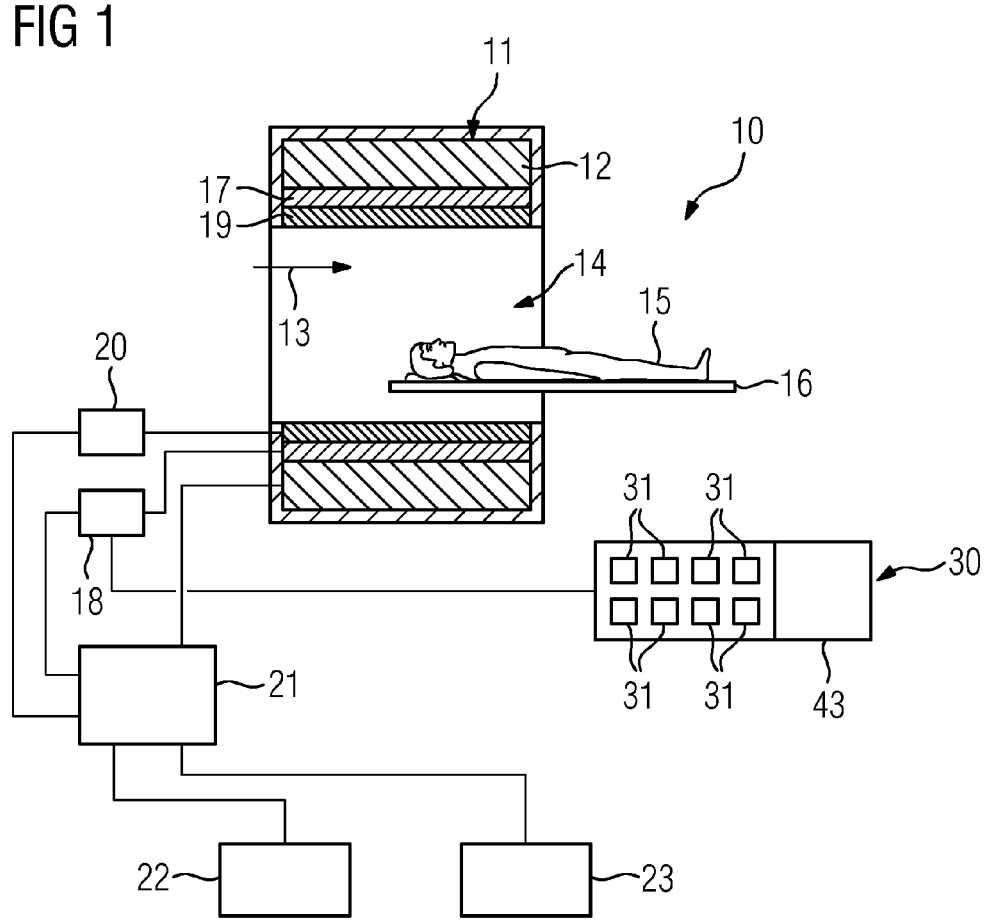
FIG. 1 shows a disclosed medical imaging device with a voltage equalization device in a schematic representation.

FIG. 1 shows a disclosed medical imaging device which in the present embodiment takes the form of a magnetic resonance imaging device 10. In an alternative embodiment, the medical imaging device can also take the form of a computed tomography device and/or a PET (positron emission tomography) device, etc.

The magnetic resonance imaging device 10 comprises a magnet unit 11 which has a main magnet 12 for generating a strong and constant main magnetic field 13. The magnetic resonance imaging device 10 also comprises a cylindrical receiving region 14 for receiving a patient 15, wherein the receiving region 14 is surrounded by the magnet unit 11 in a circumferential direction. The patient 15 can be introduced into the receiving region 14 by a patient couch 16 of the magnetic resonance imaging device 10.

The magnet unit 11 also has a gradient coil unit 17 for generating magnetic field gradients that are used for spatial encoding during an imaging process. The gradient coil unit 17 is controlled by a gradient amplifier unit 18. The magnet unit 11 also has a radio-frequency antenna unit 19 and a radio-frequency antenna control unit 20 for exciting a polarization which becomes established in the main magnetic field 13 that is generated by the main magnet 12. The radio-frequency antenna unit 19 is controlled by the radio-frequency antenna control unit 20 and radiates radio-frequency magnetic resonance sequences into an examination space which is formed by the receiving region 14. The magnetization is deflected from its position of equilibrium in this way. The radio-frequency antenna unit 19 also serves to receive magnetic resonance signals.

The magnetic resonance imaging device 10 has a control unit 21 in the form of a computing unit for the purpose of controlling the main magnet 12, the gradient amplifier unit 18 and the radio-frequency antenna control unit 20. The computing unit controls the magnetic resonance imaging device 10 centrally, e.g. by performing a predetermined imaging gradient echo sequence. Control information such as e.g. imaging parameters and reconstructed magnetic resonance images can be displayed on a display unit 22, e.g. a monitor, of the magnetic resonance imaging device 10. The magnetic resonance imaging device 10 also has an input unit 23 by which information and/or parameters can be entered by an operator during a measurement procedure.

The magnetic resonance imaging device 10 also has a voltage equalization device 30 that is provided for the purpose of equalizing voltage fluctuations, thereby allowing a voltage supply which has a voltage value that is as constant as possible during the operation of the magnetic resonance imaging device 10 (FIG. 1). In this case currently occurring voltage fluctuations of a voltage value in a supply network to which the magnetic resonance imaging device 10 is connected are equalized by the voltage equalization device 30 before they can be transferred onward to sensitive components or modules of the magnetic resonance imaging device 10, e.g. the gradient coil unit 17 or the gradient amplifier unit 18.

For this purpose the voltage equalization device 30 has a transformer unit 31 for each phase of the multiphase supply network, the individual transformer units 31 being so configured as to be structurally identical. In FIGS. 2 to 6, only one transformer unit 31, 101, 201, 301, 401 of the respective voltage equalization device 30, 100, 200, 300, 400 is illustrated in each case, wherein the functionality of all transformer units 31, 101, 201, 301, 401 of a voltage equalization device 30, 100, 200, 300, 400 is identical.

Figure 2:
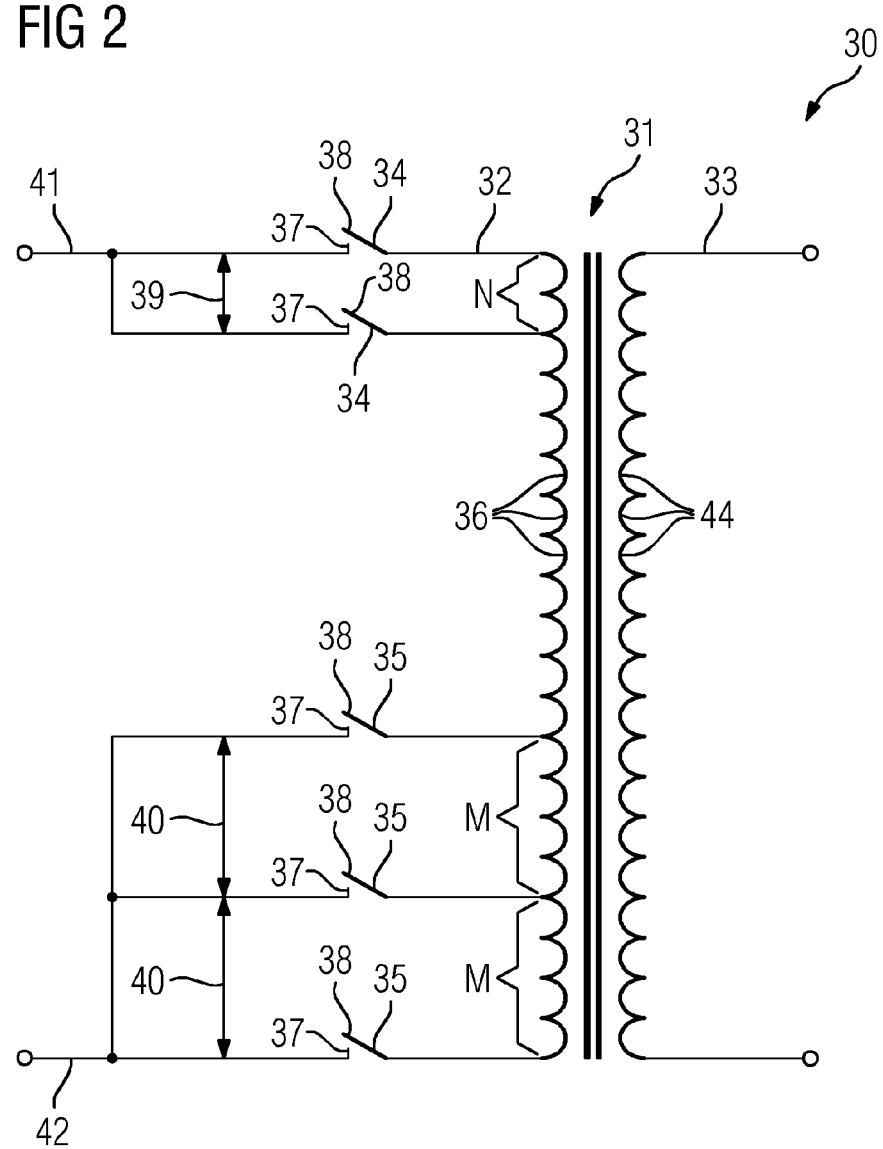
FIG. 2 shows a first embodiment variant of the voltage equalization device.

The transformer unit 31 in FIG. 2 has a primary winding unit 32 and a secondary winding unit 33. The voltage equalization device 30 also has at least three or more selection units 34, 35 which are arranged at one of the two winding units 32. In the present embodiment, the selection units 34, 35 are arranged at the primary winding unit 32.

The selection units 34, 35 are in each case designed for the purpose of switching in or switching out turns 36 of the winding unit 32 having the selection units 34, 35, such that depending on a switch position 37, 38 of the selection units 34, 35 during operation of the voltage equalization device 30 a current flows through the turns 36 that can be switched by the selection units 34, 35 or a current flow through the turns 36 that can be switched by the selection units 34, 35 is interrupted. The individual selection units 34, 35 are arranged spaced apart from one another, wherein a distance 39, 40 between two adjacently arranged selection units 34, 35 is formed by a number of turns 36 of the primary winding unit 32. In this case, a distance 39, 40 or a number N of turns 36 between two first adjacent selection units 34 is different from a distance 40 or a number M of turns 36 between two further adjacent selection units 35.

The primary winding unit 32 has an upper winding end 41 and a lower winding end 42. Two of the selection units 34 are arranged at the upper winding end 41 and three of the selection units 35 are arranged at the lower winding end 42. According to the application, the selection units 34 arranged at the upper winding end 41 of the primary winding unit 32 are separated from one another by a uniform distance 39, such that the selection units 34 arranged at the upper winding end 41 are so arranged as to be separated from one another by an identical number N of turns 36 at the primary winding unit 32. In addition, the selection units 35 arranged at the lower winding end 42 of the primary winding unit 32 are also separated from one another by a uniform distance 40, such that the selection units 35 arranged at the lower winding end 42 are so arranged as to be separated from one another by an identical number M of turns 36 at the primary winding unit 32. The number N of turns 36 between the selection units 34 arranged at the upper winding end 39 is different from the number M of turns 36 between the selection units 35 arranged at the lower winding end 42.

The number M of turns 36 between any two adjacent selection units 35 arranged at the lower winding end 42 of the primary winding unit 32 is formed as a product of a number n of the selection units 34 arranged at the upper winding end 41 and a number N of turns 36 between two adjacent selection units 34 arranged at the upper winding end 41:

$$M = n*N.$$

In the present embodiment, the number n of selection units 34 arranged at the upper winding end 41 is two and the number N of turns 36 between two adjacent selection units 34 arranged at the upper winding end 41 is two turns. The number M of turns 36 between two adjacent selection units 35 arranged at the lower winding end 42 is four turns. In the present embodiment, the total number of available turns 36 of the primary winding unit 32 is twenty turns.

A maximum of possible combinations between the two winding ends 41, 42 is thus achieved by selecting or switching in one selection units 34 arranged at the upper winding end 41 and one selection units 35 arranged at the lower winding end 42 in each case, thereby providing maximum variation in the number of turns 36 between the selection units 34 arranged and selected at the upper winding end 41 and the selection units 35 arranged and selected at the lower winding end 42, between which is present a voltage that is present at the primary unit 32 during operation. According to the application, the selection units 34, 35 have an electronically actuatable switch unit in each case. The individual switch units switch between two switch positions 37, 38 in this case, wherein one of the two switch positions 37 represents a low-impedance switch position 37 and the other of the two switch positions 38 represents a high-impedance switch position 38. If the selection units 34, 35 is in the low-impedance switch position 37, a conductive connection is established to the turns 36 that can be switched by the selection units 34, 35, and a current can flow through the turns 36 (that can be switched by the respective selection units 34, 35) of the primary winding unit 32 during the operation of the voltage equalization device 30. In this low-impedance switch position 37, the turns 36 are additionally switched in to a total number of turns between which the voltage is present in the primary winding unit 32. If the selection units 34, 35 are in the high-impedance switch position 38, a conductive connection is interrupted for the turns 36 that can be switched by the selection units 34, 35. In this high-impedance switch position 38, the turns 36 are switched out and do not contribute to the total number of turns of the primary winding unit 32.

In order to prevent short-circuits within the voltage equalization device 30, a maximum of one of the selection units 34 can be switched in at the upper winding end 41, such that only one of the two selection units 34 is in the low-impedance switch position 37. The further selection units 34 must be positioned in the high-impedance switch position 38 in this case. Likewise, a maximum of one of the selection units 35 arranged at the lower winding end 42 can be switched in and disposed in the low-impedance switch position 37. The further two selection units 35 must be positioned in the high-impedance switch position 38 in this case. Moreover, only one of the selection units 34 arranged at the upper winding end 41 and only one of the selection units 35 arranged at the lower winding end 42 must be disposed in the low-impedance switch position 37 in order to ensure an effective current flow within the primary winding unit 32.

As a result of varying the number of turns 36 which contribute to the total number of turns and at which is present the voltage that is present at the primary winding unit 32, the voltage that is present at the secondary winding unit 33 is changed relative to the voltage that is present at the primary winding unit 32. The variation of the number of turns 36 which contribute to the total number of turns is effected here by selecting a respective switch position 37, 38 for the individual selection units 34, 35. The aim here is to maintain a value that is as uniform as possible for the voltage that is present at the secondary winding unit 33.

A value or a number P representing a maximum of possible combinations of different switch positions 37, 38 at the individual selection units 34, 35 for setting a constant voltage that is present at the secondary winding unit 33 is calculated as follows:

$$P = n*m.$$

In this case n is the number of selection units 34 arranged at the upper winding end 41 and m is the number of selection units 35 arranged at the lower winding end 42, wherein the number N of turns 36 that can be switched in at the upper winding end 41 must be different here from the number M of turns that can be switched in at the lower winding end 42. In the present embodiment there are six possible combinations available for different settings of a number of turns 36 for the purpose of setting the voltage value.

The present embodiment provides combinations comprising ten turns, twelve turns, fourteen turns, sixteen turns, eighteen turns and twenty turns at the primary winding unit 32 for the purpose of setting the voltage that is present at the secondary winding unit 33. The smallest difference between the individual possible settings is two turns in this case, and the voltage can be varied by approximately 10% by switching in or switching out two turns. Furthermore, it is also conceivable for the total number of turns 36 of the primary winding unit 32 to be greater than twenty, such that a smaller equalization range for the voltage that is to be set can be achieved by switching in or switching out two turns.

For the purpose of selecting and/or setting the individual selection units 34, 35, the voltage equalization unit 30 has a monitoring unit 43 (FIG. 1). The monitoring unit 43 determines a voltage characteristic for a single phase of the multiphase supply network. On the basis of said voltage characteristic, the monitoring unit 43 determines a voltage $U_1$ that is currently present at the primary winding unit 32. For this purpose the monitoring unit 43 can have a voltage measuring unit (not shown in further detail). Subsequently, using said voltage $U_1$ that is currently present at the primary winding unit 32 and the constant reference voltage $U_2$ that is present at the secondary winding unit 33 and the constant number $W_2$ of turns 44 at the secondary winding unit 33, the monitoring unit 43 specifies a number $W_1$ of turns 36 between which is present the voltage $U_1$ that is present at the primary winding unit 32, and which are arranged between the upper winding end 41 and the lower winding end 42 of the primary winding unit 32:

$$W_1 = U_1*W_2/U_2.$$

On the basis of the voltage characteristic that has been determined and/or the number of turns $W_1$ that has been determined, the monitoring unit 43 determines and sets a switch position 37, 38 for each of the selection units 34, 35 arranged at the primary winding unit 32. In this case one selection units 34 arranged at the upper winding end 41 and one selection units 35 arranged at the lower winding end 42 is respectively selected by the monitoring unit 43 and switched in electronically by the monitoring unit 43. Provision is thus made for switching in all of the turns 36 of the primary winding unit 32 that are arranged between the selection units 34 arranged and selected and/or switched in at the upper winding end 41 and the selection units 35 arranged and selected and/or switched in at the lower winding end 42, such that the voltage $U_1$ that is present at the primary winding unit 32 is present at these turns 36. The remaining selection units 34, 35 arranged at the primary winding unit 32 are so switched by the monitoring unit 43 as to be disposed in the high-impedance switch position 38.

Furthermore, the transformer units 31 are controlled and/or regulated by the monitoring unit 43, such that as soon as only one of the selection units 34 at the upper winding end 41 is disposed in the low-impedance switch position 37, the remaining selection units 34 at the upper winding end 41 are disposed in the high-impedance switch position 38 and cannot be switched into the low-impedance switch position 37. The same also applies to the selection units 35 arranged at the lower winding end 42. As soon as only one of the selection units 35 at the lower winding end 42 is disposed in the low-impedance switch position 37 here, the remaining selection units 35 at the lower winding end 42 are disposed in the high-impedance switch position 38 and cannot be switched into the low-impedance switch position 37. In this way the monitoring unit 43 can prevent a short-circuit in the voltage equalization device 30.

The setting of the selection units 34, 35 is effected by the monitoring unit 43 for each of the transformer units 31 and/or for each phase in an analogous manner to that explained above, wherein a determination of the voltage characteristic is effected for one phase only, and the setting of the switch position 37, 38 of the selection units 34, 35 or the setting of the number of turns and hence the setting of a voltage $U_2$ that is present at the secondary winding unit 33 is effected for all transformer units 31 on the basis of said voltage characteristic that has been determined in respect of a single phase.

A currently present voltage characteristic is continuously determined by the monitoring unit 43, and the voltage $U_2$ that must be set at the secondary winding unit 33 for each phase and/or for each of the transformer units 30 is regulated on the basis of said currently present voltage characteristic. In this way the number of active turns 36 of the primary winding unit 32 can be adjusted rapidly to the currently present voltage characteristic, and the voltage $U_2$ that is present at the secondary winding unit 33 can be kept maximally constant.

Alternative embodiments of the voltage equalization device 30, 100, 200, 300, 400 are illustrated in FIGS. 3 to 6. Identical components, features and functions are generally denoted by the same reference signs. The following description is concerned only with the differences compared to the embodiment in FIGS. 1 and 2, with reference being made to the description of the embodiment shown in FIGS. 1 and 2 in respect of identical components, features and functions.

Figure 3:
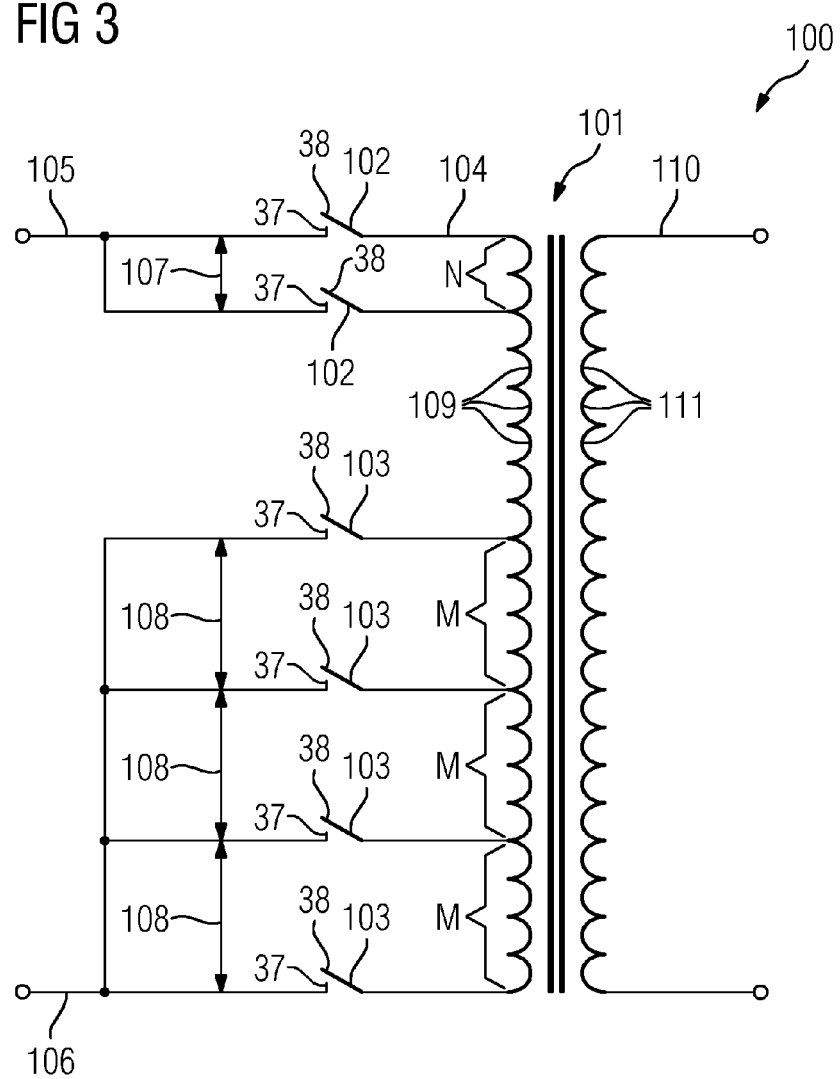
FIG. 3 shows a second embodiment variant of the voltage equalization device.

FIG. 3 shows a schematic representation of an alternative voltage equalization device 100 to that in FIG. 2. The voltage equalization device 100 differs from the voltage equalization device 30 in the description relating to FIG. 2 in respect of the number of selection units 102, 103 and the arrangement of these selection units 102, 103 at a primary winding unit 104 of a transformer unit 101 of the voltage equalization device 100.

The voltage equalization device 100 has six selection units 102, 103 in total, two of these selection units 102 being arranged at an upper winding end 105 of the primary winding unit 104 and four of these selection units 103 being arranged at a lower winding end 106 of the primary winding unit 104. In this case there is a distance 107 of two turns between the two selection units 102 arranged at the upper winding end 105. According to the condition M=n*N, the distance 108 between any two adjacent selection units 103 arranged at the lower winding end 106 is four turns. A total number of turns 109, 111 of the primary winding unit 104 and a secondary winding unit 110 is twenty turns.

In the present embodiment there is a total of eight combinations comprising six turns, eight turns, ten turns, twelve turns, fourteen turns, sixteen turns, eighteen turns or twenty turns available for setting the voltage $U_2$ that is present at the secondary winding unit 108. The smallest difference between the individual possible settings is two turns in this case.

The further embodiment of the voltage equalization device 100 corresponds to the explanations relating to the embodiment shown in FIGS. 1 and 2.

Figure 4:
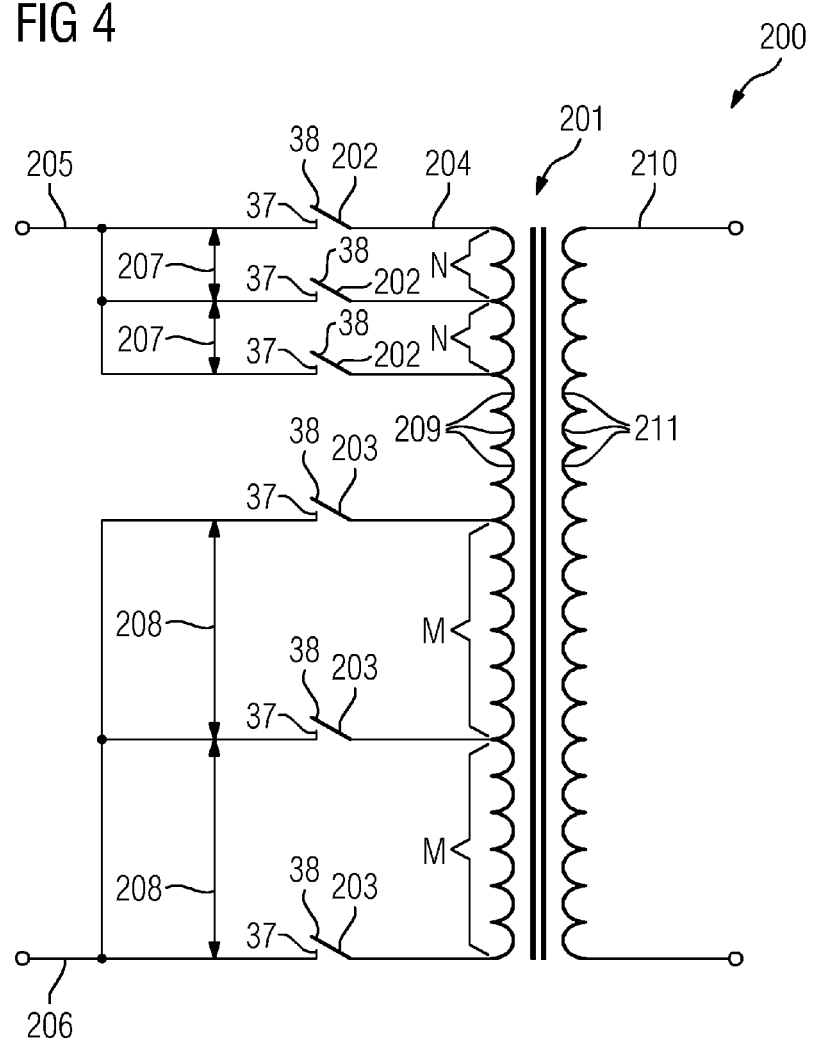
FIG. 4 shows a third embodiment variant of the voltage equalization device.

FIG. 4 shows a schematic representation of an alternative voltage equalization device 200 to that in FIGS. 2 and 3. The voltage equalization device 200 differs from the voltage equalization device 30 in the description relating to FIG. 2 in respect of the number of selection units 202, 203 and the arrangement of these selection units 202, 203 at a primary winding unit 204 of a transformer unit 201 of the voltage equalization device 200.

The voltage equalization device 200 has six selection units 202, 203 in total, three of these selection units 202 being arranged at an upper winding end 205 of the primary winding unit 204 and three of these selection units 203 being arranged at a lower winding end 206 of the primary winding unit 204. In this case there is a distance 207 of two turns between any two adjacent selection units 202 arranged at the upper winding end 205. According to the condition M=n*N, the distance 208 between any two adjacent selection units 203 arranged at the lower winding end 206 is six turns. A total number of turns 209, 211 of the primary winding unit 204 and a secondary winding unit 210 is twenty turns.

The present embodiment makes available a total of nine combinations for setting the voltage $U_2$ that is present at the secondary winding unit 210. The combinations encompass a range from four turns to twenty turns, wherein a difference between the individual possible settings is two turns or a multiple of two turns.

The further embodiment of the voltage equalization device 200 corresponds to the explanations relating to the embodiment shown in FIG. 2.

Figure 5:
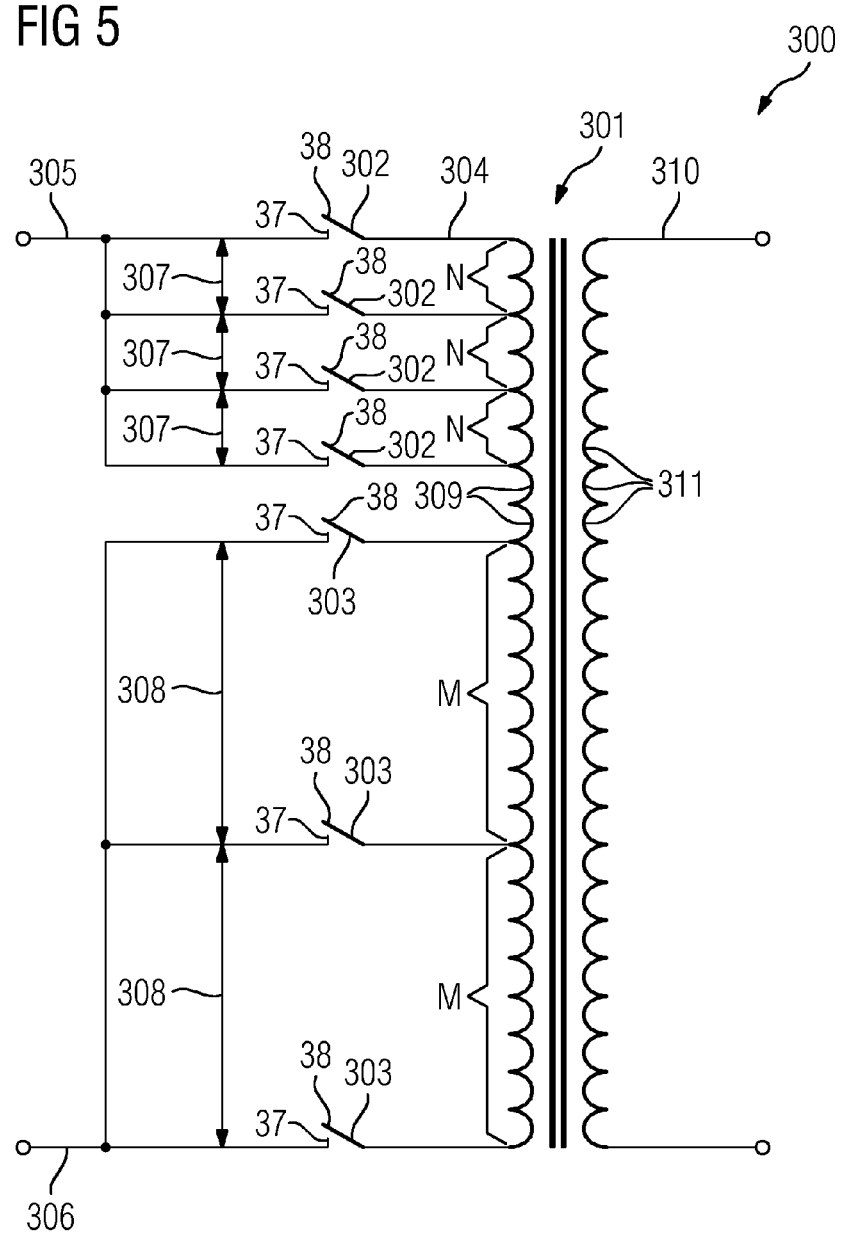
FIG. 5 shows a fourth embodiment variant of the voltage equalization device.

FIG. 5 shows a schematic representation of an alternative voltage equalization device 300 to that in FIGS. 2 to 4. The voltage equalization device 300 differs from the voltage equalization device 30 presented in the description relating to FIG. 2 in respect of the number of selection units 302, 303 and the arrangement of these selection units 302, 303 at a primary winding unit 304 of a transformer unit 301 of the voltage equalization device 300.

The voltage equalization device 300 has seven selection units 302, 303 in total, four of these selection units 302 being arranged at an upper winding end 305 of the primary winding unit 304 and three of these selection units 303 being arranged at a lower winding end 306 of the primary winding unit 304. In this case there is a distance 307 of two turns between any two adjacent selection units 302 arranged at the upper winding end 305. According to the condition M=n*N, the distance 308 between any two adjacent selection units 303 arranged at the lower winding end 306 is four turns. A total number of turns 309, 311 of the primary winding unit 304 and a secondary winding unit 310 is twenty-four turns.

The present embodiment provides a total of twelve combinations for setting the voltage $U_2$ that is present at the secondary winding unit 310. The combinations encompass a range from two turns to twenty-four turns, wherein a difference between the individual possible settings is two turns or a multiple of two turns.

The further embodiment of the voltage equalization device 300 corresponds to the explanations relating to the embodiment shown in FIG. 2.

Figure 6:
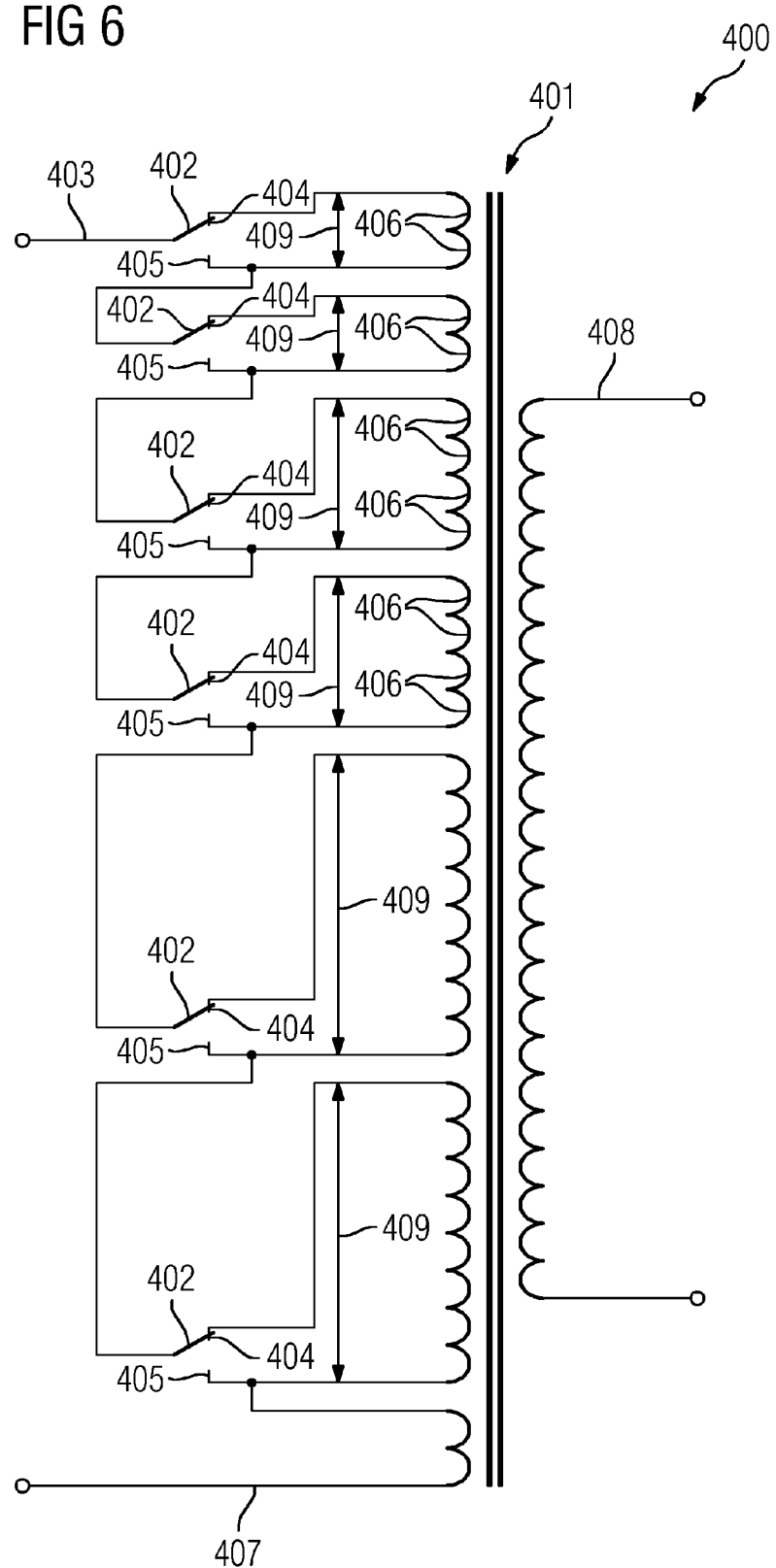
FIG. 6 shows a fifth embodiment variant of the voltage equalization device.

FIG. 6 shows a schematic representation of an alternative voltage equalization device 400 to that in FIGS. 2 to 5. The voltage equalization device 400 differs from the voltage equalization device 30 presented in the description relating to FIG. 2 in respect of the number of selection units 402 and the arrangement of these selection units 402 at a primary winding unit 403 of a transformer unit 401 of the voltage equalization device 400.

The voltage equalization device 400 has six selection units 402 in total, each of which has an electronically actuatable switch unit and/or an electronically actuatable conversion unit that switches between two low-impedance switch positions 404, 405. In a first of the two low-impedance switch positions 404 of the selection units 402, those turns 406 of the primary winding unit 403 that can be switched by the selection units 402 are switched in during operation of the voltage equalization device 400, such that the voltage $U_1$ which is present at the primary winding unit 403 during the operation of the magnetic resonance imaging device 10 is also present at the turns 406 that can be switched by this selection units 402. In a second of the two low-impedance switch positions 405 of the selection units 402, those turns 406 that can be switched by the selection units 402 are switched out during the operation of the voltage equalization device 400, such that the voltage $U_1$ which is present at the primary winding unit 403 during the operation of the magnetic resonance imaging device 10 is not present at the turns 406 that can be switched by this selection units 402. In this second switch position 405 of the selection units 402, a current flowing through the primary winding unit 403 is routed directly to the next adjacent selection units 402 in the direction of current during the operation of the magnetic resonance imaging device 10. In this way, any desired number of turns 406 can be switched in or switched out, since e.g. all selection units 402 can assume an identical switch position 404, 405.

In the present embodiment, the individual selection units 402 are arranged consecutively, such as in serial order, wherein two turns 406 that cannot be switched out are arranged at a lower winding end 407 of the primary winding unit 403. By virtue of two of the selection units 402, two turns 406 in each case are so arranged that they can be switched in or switched out at the primary winding unit 403. By virtue of two more of the selection units 402, four turns 406 in each case are so arranged that they can be switched in or switched out at the primary winding unit 403. By virtue of the remaining two selection units 402, eight turns 406 in each case are so arranged that they can be switched in or switched out at the primary winding unit 403. A distance 409 between the individual selection units 402 is $2^K$ turns 406, where K assumes values between one and three in the present embodiment. A total number of turns 406 of the primary winding unit 403 is twenty-four turns 406. A staggering that comprises distances 409 of $3^K$ turns 406 between the individual selection units 402 is also conceivable in principle.

The voltage equalization device 400 in the present embodiment has a total of twelve combinations for setting the voltage $U_2$ that is present at the secondary winding unit 408. The combinations encompass a range from two turns to twenty-four turns, wherein a difference between the individual possible settings is two turns or a multiple of two turns.

The further embodiment of the voltage equalization device 400 corresponds to the explanations relating to the embodiment in FIG. 2.

For all of the embodiments in FIGS. 2 to 6, it holds that a smallest distance 39, 40, 107, 108, 207, 208, 307, 308, 402 of turns 36, 109, 209, 309, 406 between two selection units 34, 35, 102, 103, 202, 203, 302, 303, 402 corresponds to a smallest change in respect of the setting of the voltage $U_2$ that is present at the secondary winding unit 33, 110, 210, 310, 408. The embodiments illustrated in FIGS. 2 to 6 are to be understood merely as examples. A different total number of turns 36, 44, 109, 111, 209, 211, 309, 311, 406 at the primary winding unit 32, 104, 204, 304, 403 and/or the secondary winding unit 33, 110, 210, 310, 408 and/or a different distance 39, 40, 107, 108, 207, 208, 307, 308, 409 between two adjacent selection units 34, 35, 102, 103, 202, 203, 302, 303, 402 from the embodiments presented here are/is possible at any time.

In the present embodiments illustrated in FIGS. 2 to 6, the distances 39, 40, 107, 108, 207, 208, 307, 308, 409 between the individual selection units 34, 35, 102, 103, 202, 203, 302, 303, 402 comprise a number N, M of $2^K$ turns 36, 109, 209, 309, 406. A distance 39, 40, 107, 108, 207, 208, 307, 308, 409 comprising $3^K$ turns 36, 109, 209, 309, 406 between the individual selection units 34, 35, 102, 103, 202, 203, 302, 303, 402 is also possible at any time.

The invention claimed is:

1. A voltage equalization device for equalizing voltage fluctuations in a voltage supply, comprising:
a transformer unit comprising a primary winding unit and a secondary winding unit; and
a plurality of selection units arranged at one of the primary and the secondary winding units for switching in or switching out turns of the winding unit having the selection units,
wherein two adjacent selection units are arranged to be separated from one another by a distance comprising a number of turns, and
wherein a first number of turns between two first adjacent selection units is different from a second number of turns between two further adjacent selection units.

2. The voltage equalization device as claimed in claim 1, wherein the selection units are arranged at the primary winding unit.

3. The voltage equalization device as claimed in claim 1, wherein the winding unit having the selection units has an upper winding end and a lower winding end, and wherein at least two of the selection units are arranged at the upper winding end and at least two of the selection units are arranged at the lower winding end.

4. The voltage equalization device as claimed in claim 3, wherein the selection units arranged at the upper winding end are separated from one another by a first identical number of turns, wherein the selection units arranged at the lower winding end are separated from one another by a second identical number of turns, and wherein the first number of turns is different from the second number of turns.

5. The voltage equalization device as claimed in claim 4, wherein the second identical number of turns comprises a number of selection units arranged at the upper winding end multiplied by the first identical number of turns.

6. The voltage equalization device as claimed in claim 3, wherein the selection units comprise an electronically actuatable switch unit that can be switched between a low-impedance switch position and a high-impedance switch position.

7. The voltage equalization device as claimed in claim 6, wherein only one of the selection units arranged at the upper winding end and only one of the selection units arranged at the lower winding end is disposed in the low-impedance switch.

8. The voltage equalization device as claimed in claim 3, wherein a maximum number of combinations for different numbers of turns between the selection units comprises a number of selection units arranged at the upper winding end multiplied by a number of selection units arranged at the lower winding end.

9. The voltage equalization device as claimed in claim 1, wherein the selection units comprise an electronically actuatable switch unit that can be switched between two low-impedance switch positions.

10. The voltage equalization device as claimed in claim 1, wherein an arbitrary number of selection units from the selection units can be concurrently switched to a switch position for establishing a conductive connection to turns using the selection units.

11. The voltage equalization device as claimed in claim 1, further comprising a monitoring unit for determining a voltage characteristic at the winding unit having the selection units and for setting a switch position for the selection units.

12. The voltage equalization device as claimed in claim 11, wherein the monitoring unit determines the voltage characteristic for one phase of a multiphase supply network and sets a voltage for phases of the multiphase supply network based on the voltage characteristic determined for the one phase.

13. The voltage equalization device as claimed in claim 11, wherein the monitoring unit regulates the voltage by selecting a respective switch position of the selection units as a function of the voltage characteristic determined for the one phase.

14. A medical imaging device, comprising:
a voltage equalization device as claimed in claim 1.

15. The medical imaging device as claimed in claim 14, wherein the voltage equalization device is adapted to set a constant voltage for a gradient coil unit.

16. The medical imaging device as claimed in claim 14, wherein the medical imaging device comprises a magnetic resonance imaging device.

* * * * *